United States Patent [19]

Homann

[11] Patent Number: 4,665,241

[45] Date of Patent: May 12, 1987

[54] METHOD FOR PROCESSING SUBSTITUTED 1,3-DIOLS OF LOW WATER SOLUBILITY

[75] Inventor: Walter K. Homann, Dülmen, Fed. Rep. of Germany

[73] Assignee: Hüls Aktiengesellschaft, Marl, Fed. Rep. of Germany

[21] Appl. No.: 861,760

[22] Filed: May 9, 1986

Related U.S. Application Data

[63] Continuation-in-part of Ser. No. 747,848, Jun. 24, 1985, abandoned.

[30] Foreign Application Priority Data

Sep. 6, 1984 [DE] Fed. Rep. of Germany ....... 3432719

[51] Int. Cl.$^4$ ...................... C07C 31/20; C07C 29/86; C07C 29/80; C07C 29/74
[52] U.S. Cl. .................................. 568/868; 568/854; 568/919
[58] Field of Search .................. 568/868, 854, 919

[56] References Cited

U.S. PATENT DOCUMENTS

| | | | |
|---|---|---|---|
| 2,626,284 | 1/1953 | Smith | 568/919 |
| 2,761,881 | 9/1956 | Rosin | 568/854 |
| 2,865,819 | 12/1958 | Hagemeyer et al. | 568/854 |
| 3,340,312 | 9/1967 | Duke et al. | 568/854 |
| 3,359,335 | 12/1967 | Roming | 568/919 |
| 3,939,216 | 2/1976 | Wright | 568/854 |
| 3,989,763 | 11/1976 | Fujii et al. | 568/919 |

*Primary Examiner*—J. E. Evans
*Attorney, Agent, or Firm*—Quaintance, Murphy & Presta

[57] ABSTRACT

Crude product substituted 1,3-diols obtained by aldolization and subsequent hydrogenation are treated at elevated temperatures with at least sufficient basic additives to reduce the saponification number to zero. Thereupon, the saponified product is reacted with 5 to 30% water and possibly cooled to 1° to 30° C. The aqueous phase is separated mechanically, and following the separation and addition of 5 to 30% water the organic phase is adjusted to a pH of 8.0 to 10.5. A second aqueous phase is removed and, thereupon, the monovalent alcohol is removed by distillation from the second organic phase. Again the pH value of the second organic phase is set at 8.0 to 10.5 and the 1,3-diol is recovered by fractionation.

9 Claims, No Drawings

METHOD FOR PROCESSING SUBSTITUTED 1,3-DIOLS OF LOW WATER SOLUBILITY

This application is a continuation-in-part of application Ser. No. 747,848, filed June 24, 1985, now abandoned.

CROSS-REFERENCE TO A RELATED APPLICATION

Applicant claims priority under 35 USC 119 for application No. P 34 32 719.3, filed Sept. 6, 1984, in the Patent Office of West Germany.

BACKGROUND OF THE INVENTION

The field of the invention is substituted 1,3-diols and the invention is particularly concerned with the purification of these diols.

An Example of these 1,3-diols is trimethylpentanediol (2,2,4-trimethyl-1,3-pentanediol) as disclosed in the Kirk-Othmer, Encyclopedia of Chemical Technology, Vol. 10 (1966) pp. 676-680 and the Kirk-Othmer, Concise Encyclopedia of Chemical Technology (1985) under the section "Other Glycols", p. 568. Other substituted 1,3-diols are disclosed in U.S. Pat. No. 2,643,262 such as ethylhexanediol (2-ethyl-1,3-hexanediol), and propylheptanediol (2-propyl-1,3-heptanediol).

The state of the art of purifying these substituted 1,3diols may be ascertained by reference to U.S. Pat. No. 2,865,819, West German Pat. No. 967,552 and Japanese Pat. No. 69/10767, the disclosures of which are incorporated herein by reference.

In the present invention the term saponification number is used and this term is defined in Kirk-Othmer, supra, Vol. 1 (1963) at page 302 as the number of miligrams of potassium hydroxide required for the saponification and neutralization of one gram of sample.

The substituted 1,3-diols of the present invention have the general formula:

$$R^1-\underset{\underset{OH}{|}}{CH}-CR_2-\underset{\underset{OH}{|}}{CH}-R$$

where R=alkyl and/or hydrogen, R'=alkyl.

These substituted 1,3-diols of the general formula are prepared by aldolization reactions with ensuing hydrogenation according to the following equation:

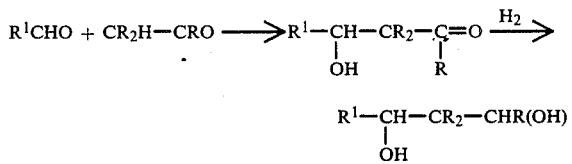

$$R^1CHO + CR_2H-CRO \longrightarrow R^1-\underset{\underset{OH}{|}}{CH}-CR_2-\underset{\underset{R}{|}}{C}=O \xrightarrow{H_2}$$

$$R^1-\underset{\underset{OH}{|}}{CH}-CR_2-CHR(OH)$$

Frequently esters are obtained as by products in the above reaction which must be removed by distillation separation. Product losses are incurred in this distillation separation and the separation requires a more than proportional cost.

Esters are saponifiable in principle but new problems arise in crude products so treated. These problems include partial product decompositions during distillation. Japanese Pat. No. 69/10767 recommends using extractants such as di-n-butylether in the case of water-soluble 2,2-dimethyl-1,3-propanediol to avoid these problems. Again, pretreatment by means of a falling-film evaporator is recommended to separate salts and substances of higher boiling points accumulating during the synthesis. In the process of U.S. Pat. No. 2,865,819, water and tetralin are added to separate neopentyl glycol from the saponification salts in several stages. Further, West German Pat. No. 967,552 discloses using ion exchangers to remove salts contained in the crude product.

Some of the drawbacks of these methods are that they require accessory substances which must be removed in energy-intensive manner and/or which are expensive or leave out of consideration losses of valuable materials.

SUMMARY OF THE INVENTION

Having in mind the limitations of the prior art it is an object of the present invention to improve the efficiency of the process for purifying substituted 1,3-diols.

This object is achieved by treating the crude product obtained by aldolization and subsequent hydrogenation and having a given positive saponification number at an elevated temperature with sufficient basic additives to reduce the saponification number to at least zero.

Thereupon the saponified product is reacted with 5 to 30% water and possibly cooled to 1° to 30° C. The aqueous phase is separated mechanically, and following the separation and addition of 5 to 30% water the organic phase is adjusted to a pH of 8.0 to 10.5. The aqueous phase is removed again and thereupon the monovalent alcohol is removed by distillation. Again the pH value is set at 8.0 to 10.5 and the 1,3-diol is obtained by fractional distillation.

DESCRIPTION OF THE PREFERRED EMBODIMENTS

Substituted 1,3-diols having low water solubility can be processed in surprising and problem free manner provided the crude product is treated first in relation to the given saponification number of the crude product to reduce it to at least zero. The crude product is treated at an elevated temperature, in general between 80° and 130° C., with at least sufficient basic additives to reduce the saponification number to zero, and then the saponified product is reacted with 5 to 30%, preferably 10 to 20% water. The aqueous phase is separated mechanically. Following the separation, the organic phase upon addition of water is adjusted to a pH of 8.0 to 10.5, preferably 8.5 to 9.5, and the aqueous phase is removed again. Following separation of the monovalent alcohols, a pH of 8.0 to 10.5, preferably 8.5 to 9.5 is adjusted again in the ensuing distillation. A quantity of basic additive less than that corresponding to the saponification number merely results in a minor reduction of the problems enumerated for the prior art. Illustratively alkali hydroxides and alkali earth hydroxides, as well as ammonia or amines, are useful as basic additives.

Preferably the reaction is carried out at as high a temperature as possible, as a rule between 80° and 130° C., preferably about 10° C. below the boiling point of the low boiling point substance contained in the crude discharge. Examples of these low boiling point substances include monofunctional alcohols generated when the carbonyl compounds are hydrogenated. However, when longer reaction times are accepted, the treatment is possible also at substantially lower temperatures. When the saponification is carried out in the range of the low boiling-point substance, processing with reflux is advised.

The concentration of the basic additive cannot be arbitrarily reduced as otherwise the reaction will be unnecessarily delayed. Concentrations of illustratively 10 to 50% of the solutions were found to be appropriate for practice.

Similar conditions apply in the "neutralization" to the above stated pH range. Inorganic acids such as sulfuric acid or phosphoric acid and ion exchangers are suitable to adjust the pH value.

Following saponification but before adjusting the pH, it is desirable to add 5 to 30% water so that the pH adjustment can take place without problems. Whereas on the one hand, depending on the concentration of the liquor, frequently there is inadequate phase separation for a lesser addition of water, on the other hand the presence of higher amounts of water results in undesirably high losses of the valuable substances. Preferably the minimization of product losses during the separation using suitable separating means is carried out only after a corresponding cooling to 1° to 30° C.

The desired result is obtained both for batchwise operation and for continuous operation.

SPECIFIC EXAMPLES (a) 500 g of a crude trimethylpentanediol (2,2,4-trimethyl-1,3-pentanediol) with a saponification number of 7.5 are stirred together with 6.5 g of 50% NaOH solution at 90° C. and then cooled with 100 g water to 20° C. to form aqueous and organic phases. Following addition of 100 g of water, the organic phase is set at a pH of 9 by dosing with 10% sulfuric acid to form second aqueous and organic phases. Following the separation at normal pressure of the isobutanol contained in the second organic phase, the trimethylpentanediol is fractionated in vacuum by batchwise adding concentrated sulfuric acid so that a pH of about 9 is maintained in the sump.

Referred to the trimethylpentanediol contained in the crude product, 97% of trimethylpentanediol with a purity of 99.2% is obtained.

Comparable values are obtained when using potassium hydroxide, calcium hydroxide and trioctylamine as the bases and phosphoric acid and also the ion exchanger Lewatit SPC 108 for "neutralization". A pure product with 98.8 to 99.8% is obtained in a range of trimethylpentanediol yields of 96 to 99%.

(b) 3 kg of a crude 2-ethyl-1,3-hexanediol (ethylhexanediol) with a saponification number of 8.5 are processed with 80 g of a 25% NaOH solution at 80° C. as in Example (a).

Referred to the ethylhexanediol contained in the crude product, 99% of ethylhexanediol with a purity of 99.3% is obtained.

(c) 3 kg of a crude 2-propyl-1,3-heptanediol (propylheptanediol) with a saponification number of 12.6 are processed with 300 g of a 10% NaOH solution at 100° C. as in Example (a).

Referred to the propylheptanediol contained in the crude product, 98% of propylheptanediol with a purity of 98.9% is obtained.

What I claim is:

1. In the method of purifying substituted 1,3-diols having the general formula

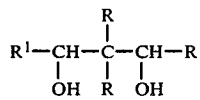

prepared by aldolization reactions with ensuing hydrogenation to form a crude product having a given positive saponification number according to the following equation:

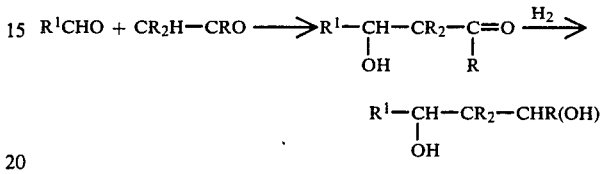

wherein R=alkyl or hydrogen, and $R^1$=alkyl, the improvement comprising:
   (a) treating said crude product at an elevated temperature with at least sufficient basic additive to reduce said saponification number to zero and produce a saponified product;
   (b) mixing said saponified product with about 5 to 30% water by weight and forming first aqueous and first organic phases;
   (c) mechanically separating said first aqueous phase from said first organic phase;
   (d) adding about 5 to 30% water by weight to said first organic phase, adjusting the resulting mixture to a pH of 8.0 to 10.5 and forming second aqueous and organic phases;
   (e) mechanically separating said second aqueous phase from said second organic phase;
   (f) separating monovalent alcohol by-product from said second organic phase by distillation;
   (g) adjusting the pH value of said monovalent alcohol free second organic phase to 8.0 to 10.5; and
   (h) recovering said substituted 1,3-diols by fractional distillation.

2. The method of claim 1, wherein step (b) further comprises cooling to 1° to 30° C.

3. The method of claim 2, wherein step (d) has a pH of 8.5 to 9.5.

4. The method of claim 3, wherein step (g) has a pH of 8.5 to 9.5.

5. The method of claim 2, wherein step (g) has a pH of 8.5 to 9.5.

6. The method of claim 1, wherein said elevated temperature of step (a) is 80° to 130° C.

7. The method of claim 6, wherein said basic additive is selected from the group consisting of alkali hydroxides, alkali earth hydroxides, ammonia and amines.

8. The method of claim 7, wherein said basic additive has a concentration of 10 to 50% by weight in water.

9. The method of claim 6, wherein said substituted 1,3-diols are selected from the group consisting of 2,2,4-trimethyl-1,3-pentanediol, 2-ethyl-1,3-hexanediol and 2-propyl-1,3-heptanediol.

* * * * *